US007818180B2

(12) United States Patent
Riff

(10) Patent No.: US 7,818,180 B2
(45) Date of Patent: Oct. 19, 2010

(54) PERSONALIZATION SOFTWARE FOR IMPLANTED MEDICAL DEVICE PATIENTS

(75) Inventor: Kenneth M. Riff, Orono, MN (US)

(73) Assignee: Medtronic, Inc., Minneapolis, MN (US)

( * ) Notice: Subject to any disclaimer, the term of this patent is extended or adjusted under 35 U.S.C. 154(b) by 1293 days.

(21) Appl. No.: 10/135,908

(22) Filed: Apr. 29, 2002

(65) Prior Publication Data

US 2003/0204413 A1 Oct. 30, 2003

(51) Int. Cl.
*G06Q 10/00* (2006.01)
*G06Q 50/00* (2006.01)
(52) U.S. Cl. .................. 705/2; 705/1; 705/3; 705/4; 600/300; 607/60; 709/203; 709/224; 128/903; 128/904
(58) Field of Classification Search ............. 705/1–4; 600/300; 607/60; 709/203, 224; 128/903, 128/904
See application file for complete search history.

(56) References Cited

U.S. PATENT DOCUMENTS

| | | | |
|---|---|---|---|
| 4,476,868 A | 10/1984 | Thompson | 128/419 |
| 5,052,388 A | 10/1991 | Sivula et al. | 128/419 |
| 5,345,362 A | 9/1994 | Winkler | 361/681 |
| 5,540,232 A | 7/1996 | Laney et al. | 128/697 |
| 5,542,420 A | 8/1996 | Goldman et al. | 128/630 |
| 5,740,252 A | 4/1998 | Minor et al. | 380/49 |
| 5,862,325 A | 1/1999 | Reed et al. | 395/200.31 |
| 5,915,001 A | 6/1999 | Uppaluru | 379/88.22 |
| 5,933,827 A | 8/1999 | Cole et al. | 707/10 |
| 5,943,496 A | 8/1999 | Li et al. | 395/685 |
| 5,949,419 A | 9/1999 | Domine et al. | 345/349 |
| 5,951,485 A | 9/1999 | Cyrus et al. | 600/523 |
| 5,963,968 A | 10/1999 | Warmus et al. | 707/517 |
| 5,966,705 A | 10/1999 | Koneru et al. | 707/9 |
| 6,018,768 A | 1/2000 | Ullman et al. | 709/218 |
| 6,029,182 A | 2/2000 | Nehab et al. | 707/523 |
| 6,035,330 A | 3/2000 | Astiz et al. | 709/218 |
| 6,063,028 A | 5/2000 | Luciano | 600/300 |
| 6,076,166 A | 6/2000 | Moshfeghi et al. | 713/201 |
| 6,081,835 A | 6/2000 | Antcliff et al. | 709/217 |
| 6,085,165 A | 7/2000 | Ulwick | 705/7 |
| 6,085,229 A | 7/2000 | Newman et al. | 709/203 |
| 6,088,717 A | 7/2000 | Reed et al. | 709/201 |
| 6,101,486 A | 8/2000 | Roberts et al. | 705/27 |
| 6,112,192 A | 8/2000 | Capek | 705/59 |
| 6,115,709 A | 9/2000 | Gilmour et al. | 707/9 |
| 6,125,385 A | 9/2000 | Wies et al. | 709/203 |
| 6,128,663 A | 10/2000 | Thomas | 709/228 |

(Continued)

OTHER PUBLICATIONS

Locke, Christopher, "Personalization: The Unanticipated Revolution," © 1999 Public Relations Society of American (www.prsa.org). From: http://www.bmacolorado.com/events/feb00_article 2.html.

*Primary Examiner*—Gerald J. O'Connor
*Assistant Examiner*—Llnh Michelle Le

(57) ABSTRACT

A system for on-line psycho-physiological profiling and support implementing a personalization engine operating in a plurality of network systems. An implanted medical device (IMD) in data communication with the personalization engine provides physiological, therapy and diagnostic data pertinent to the patient. Based on one or a combination of explicit, implicit and transactional input from the patient and in consideration of the IMD data underlying therewith, the patient is guided to consult with the most pertinent database.

19 Claims, 5 Drawing Sheets

U.S. PATENT DOCUMENTS

| | | | |
|---|---|---|---|
| 6,131,164 A | 10/2000 | Parker | 713/201 |
| 6,141,653 A | 10/2000 | Conklin et al. | 705/80 |
| 6,141,666 A | 10/2000 | Tobin | 707/513 |
| 6,151,707 A | 11/2000 | Hecksel et al. | 717/11 |
| 6,154,783 A | 11/2000 | Gilmour et al. | 709/245 |
| 6,161,126 A | 12/2000 | Wies et al. | 709/203 |
| 6,163,794 A | 12/2000 | Lange et al. | 709/202 |
| 6,167,441 A | 12/2000 | Himmel | 709/217 |
| 6,192,382 B1 | 2/2001 | Lafer et al. | 707/513 |
| 6,205,472 B1 | 3/2001 | Gilmour | 709/206 |
| 6,209,007 B1 | 3/2001 | Kelley et al. | 707/513 |
| 6,219,680 B1 | 4/2001 | Bernardo et al. | 707/501 |
| 6,222,537 B1 | 4/2001 | Smith et al. | 345/333 |
| 6,236,395 B1 | 5/2001 | Sezan et al. | 345/328 |
| 6,247,031 B1 | 6/2001 | Sugiura et al. | 707/526 |
| 6,247,032 B1 | 6/2001 | Bernardo et al. | 707/530 |
| 6,289,244 B1 | 9/2001 | Conley et al. | 607/27 |
| 6,290,646 B1 | 9/2001 | Cosentino et al. | 600/300 |
| 6,497,655 B1 * | 12/2002 | Linberg et al. | 600/300 |
| 6,735,479 B2 * | 5/2004 | Fabian et al. | 607/60 |
| 6,974,413 B2 * | 12/2005 | Bardy | 600/300 |
| 7,058,453 B2 * | 6/2006 | Nelson et al. | 607/60 |
| 7,082,334 B2 * | 7/2006 | Boute et al. | 607/60 |
| 7,156,808 B2 * | 1/2007 | Quy | 600/300 |
| 7,370,004 B1 * | 5/2008 | Patel et al. | 705/14 |
| 2001/0025137 A1 | 9/2001 | Webb et al. | 600/300 |
| 2001/0039504 A1 | 11/2001 | Linberg et al. | 705/3 |
| 2001/0051765 A1 | 12/2001 | Walker et al. | 600/300 |
| 2003/0187683 A1 * | 10/2003 | Kirchhoff et al. | 705/1 |
| 2003/0208588 A1 * | 11/2003 | Segal | 709/224 |

* cited by examiner

PERSONALIZATION SOFTWARE FOR IMPLANTED MEDICAL DEVICE PATIENTS

FIELD OF THE INVENTION

The invention relates to a system for on-line psycho-physiological parameter assessment to profile a patient with an implanted medical device (IMD) to thereby provide information, counsel and medical support. More specifically, the invention relates to a personalization engine operating on one or more websites and having data communications with the IMD to enable an information source tailored to the patient.

BACKGROUND OF THE INVENTION

Personalization of a website depends on gathering data about a specific user. The data typically comes in three forms, explicit, implicit and transactional data. Explicit data includes data such as the user indicating choices on a particular subject. Explicit data also includes data that traces and records the website that the user visits. Generally, explicit data reflects specific user choices, while implicit data attempts to infer the user's likes and dislikes from the user's actions.

On the Internet, consumer behavior may be predicted using both explicit and implicit information to deliver a more individualized experience to the user. Personalization falls into two broad categories, rule-based and collaborative. A rule-based system utilizes generally understood patterns of behavior to propose appropriate matches. For example, in an on-line merchandising application, this might take the form of offering a selection of products, to someone purchasing a related product. The collaborative approach is a tool that discovers correlations in large bodies of data to predict likely affinities or choices.

Various methods and systems for customizing consumer needs for products and services have been proposed. In an exemplary disclosure, U.S. Pat. No. 6,141,666 to Tobin discloses a server-based communication system that provides dynamic customization of hypertext tagged documents presented to clients accessing the system. The customization pertains to the content of the documents based on specific requirements of a class to which the clients belong to. This class may be defined by an entity of the source, which refers the client to the system. The system utilizes a database, that dynamically retrieves stored data in response to the server software tool, which configures the data into hypertext tagged documents. The system utilizes a dynamic token scheme to pass the identity of the referring network site from document to document to eventually identify documents accessed by the client through the hypertext tags.

U.S. Pat. No. 6,128,663 to Thomas discloses improved techniques for customizing information collected from a content server through a network to a user of a computer system. The information is customized in accordance with demographic classifications, user interests or preferences. The customization process may involve advertising using banners targeted to the user. The customization can also involve altering portions of a web page to be displayed to the user so that the web page is more effective or desirable for the user. In addition to customization of the information to be displayed to the user, the invention also provides techniques for obtaining demographic information about the user of the computer system, such that the demographic information may be transferred to the content provider such that the content provider would have knowledge about the user.

U.S. Pat. No. 6,115,709 to Gilmour et al. discloses a method of constructing a user knowledge profile. The method includes distinct public and private portions with different access restrictions and assignment of confidence level to content within an electronic document. The document is associated with a user such as, for example, the author of the document. The content may be potentially indicative of the knowledge base of the user. The content is then stored in either the public or private portion of the user knowledge profile, dependent upon whether the confidence level exceeds or falls below a predetermined threshold level. The public portion of the user knowledge profile is freely accessible by third parties, while the private portion is placed under restricted access.

U.S. Pat. No. 6,247,031 B1 to Bernardo et al. discloses an automated system for approving website content. The system includes software with prestored templates comprising html formatting code, text fields and formulas. A user is directed to select features and options desired for the website. Further, based on these selections, the tool prompts the user to supply data to populate fields of the templates determined by the tool to correspond to the selected features and options.

U.S. Pat. No. 6,209,007 B1 to Kelley et al. discloses a web internet screen customizing system, specifically, a process for creating a customized web page containing information from other web pages that is accessible by client computer from an inner or internet site is disclosed.

U.S. Pat. No. 6,167,441 to Himmel discloses a customization of web pages based on requestor type. Specifically, customized internet content is provided by requesting client device using an intercepting agent based on the capabilities of the requesting client. The agent typically at the web server to which the client requests is directed intercepts a request made by a requesting client device for a file from the web server. The agent detects client device capability information about the requesting client device, such as display or memory capabilities. The client request is redirected to a uniform resource locator (URL) according to the detected client device capability information to retrieve a version of the requested file.

U.S. Pat. No. 6,289,244 B1 to Conly et al. discloses a self-audit system for use in managing and monitoring measurements acquired by an implantable medical device in a period of time. The self-audit system includes programming one or more valid ranges for one or more measurements acquired in an implantable medical device, acquiring one or measurements in an implantable medical device and comparing the one or more measurements to their associated valid ranges. The information is recorded if it is not within its associated valid range, and displaying a warning message if a measurement is not within the associated valid range.

U.S. Pat. No. 6,063,028 to Luciano discloses an automated treatment selection method. Specifically, a method for facilitating choosing a treatment or treatment regime and for predicting the outcome of a treatment for it is ordered, which is diagnosed and monitored or other appropriately trained and licensed professional based upon the symptoms experienced by a patient. In a preferred embodiment, one method for predicting patient response includes performing at least one measurement of a symptom on a patient and measuring that symptom to derive a baseline patient profile. A set of a plurality of predictor variables defines the data of the baseline patient profile wherein the set of predictor variables includes predictive symptoms and a set of treatment options. Further, the invention enables to derive a model that represents the relationship between patient response and the set of predictor variables. The model is then implemented to predict the response of the patient to a treatment.

The above-described methods, apparatus and process are implemented using preferably keystrokes or a mouse and standard interface with a web browser to access a website. The website may consist of back-end data or modules, such as educational modules, links to other websites, historical data, or any kind of other source of back-end data. Generally, the user may access documents, video and audio feedbacks and links to other websites. Further, using these tools, a user may interact with a site that is sufficiently intelligent to select the right information tailored to the interests of the user.

Some websites include personalization engines built into them which look at specific interactions that a person is having and look at the keystrokes or the mouse strokes or any other explicit data that is coming in. Based on those explicit interactions, the system may be able to pull up certain background data that is specific to the person. For example, the person may elect to see an educational module and the personalization engine will search for the information and present it to the browser. Although personalization engines are used to identify consumer preferences, patients with implanted devices have highly specialized needs as it relates to device data. Current personalization engines do not appear to serve those needs.

Accordingly, there is a need for a personalization engine that is responsive to data collected from implanted medical devices (IMDs), including peripheral or external devices in communication with IMDs such that information relating to the performance of the IMD, delivered therapy information, as well diagnostic information could be presented in a manner that is tailored to the needs, concerns and interests of the patient.

SUMMARY OF THE INVENTION

Implanted medical device (IMD) data is integrated with interactive website systems including a personalization engine to provide tailored information, training, psychosocial support and counsel to patients with IMDs.

In one aspect of the invention, a system-operated questionnaire assesses the patient's concerns to guide to a most useful source of information including recommendations.

In another aspect of the invention, one or a combination of explicit and implicit input from the patient are analyzed to guide the patient to the most appropriate information source consistent with the medical condition indicated by the IMD.

In yet another aspect of the invention, a personalization engine is integrated with IMD data to inform, educate, warn or otherwise counsel the patient on the basis of an automatic assessment of data obtained from the IMD in the patient.

Yet another aspect of the invention includes a network-enabled interactive system for use in chronic patient management. Specifically, robust networks with various databases are integrated with IMDs in patients to enable seamless communication between patients, healthcare providers and other support groups and communities.

DESCRIPTION OF THE PREFERRED EMBODIMENT

Figure 1:
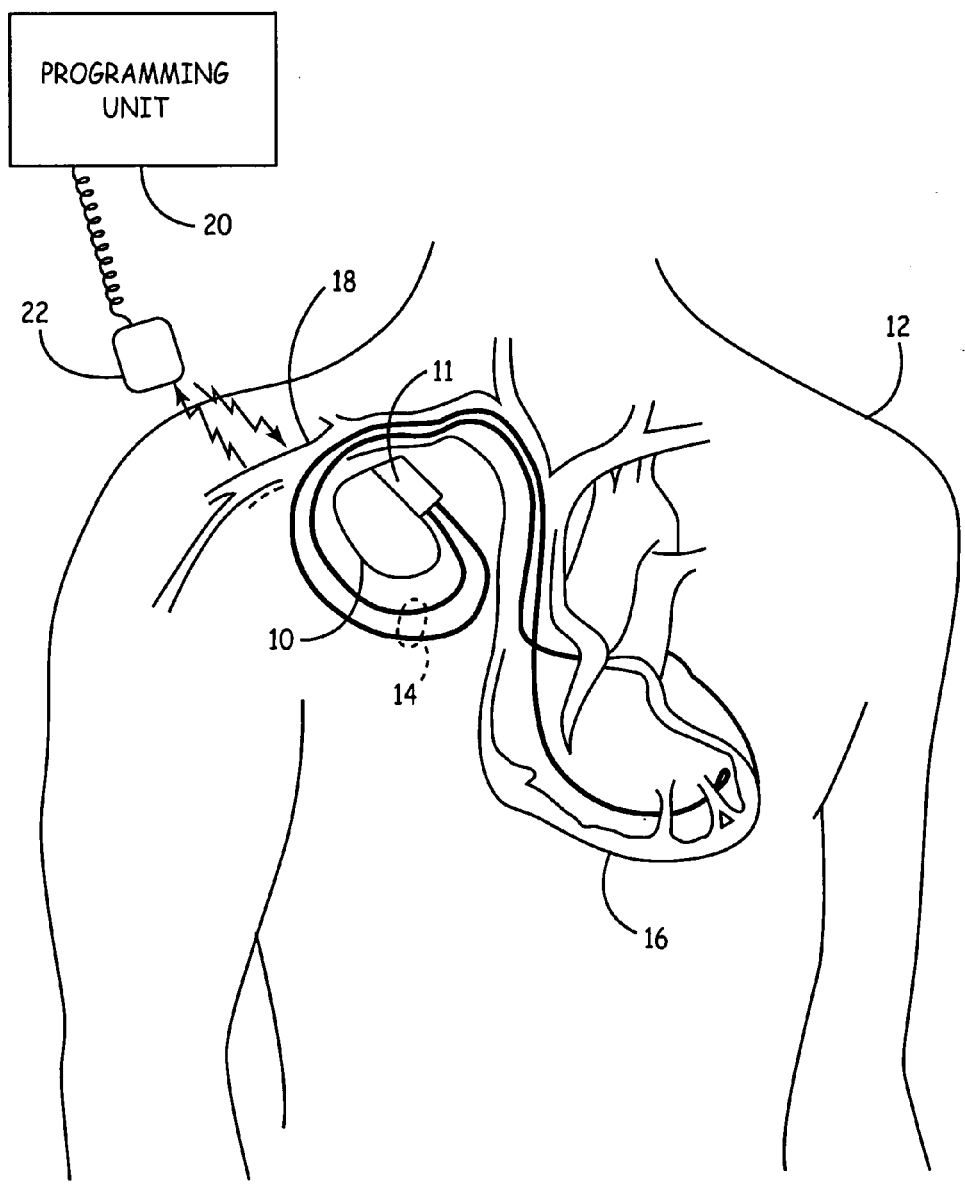
FIG. 1 is an illustration of a body-implantable device system in accordance with one embodiment of the invention, including a hermetically sealed device implanted in a patient and an external programming unit.

FIG. 1 is an illustration of an implantable medical device system adapted for use in accordance with prior art practice. The medical device system shown in FIG. 1 includes an implantable medical device (IMD) 10, for example, a pacemaker, which has been implanted in patient 12. In accordance with conventional practice in the art, IMD 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 are electrically coupled to IMD 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be practiced in connection with numerous other types of implantable medical device systems, including any application in which it is desirable to provide a communication link between two physically separated components, such as may occur during transtelephonic monitoring.

Also depicted in FIG. 1 is an external programming unit 20 for non-invasive communication with IMD 10 via uplink and downlink communication channels 24, to be hereinafter described in further detail. Associated with programming unit 20 is a programming head 22, in accordance with conventional medical device programming systems, for facilitating two-way communication between IMD 10 and programmer 20. In many known implantable device systems, a programming head such as that depicted in FIG. 1 is positioned on the patient's body over the implant site of the device, such that one or more antennae within the head can send RF signals to, and receive RF signals from, an antenna disposed within the hermetic enclosure of the implanted device or disposed within the connector block of the device, in accordance with common practice in the art.

Figure 2:
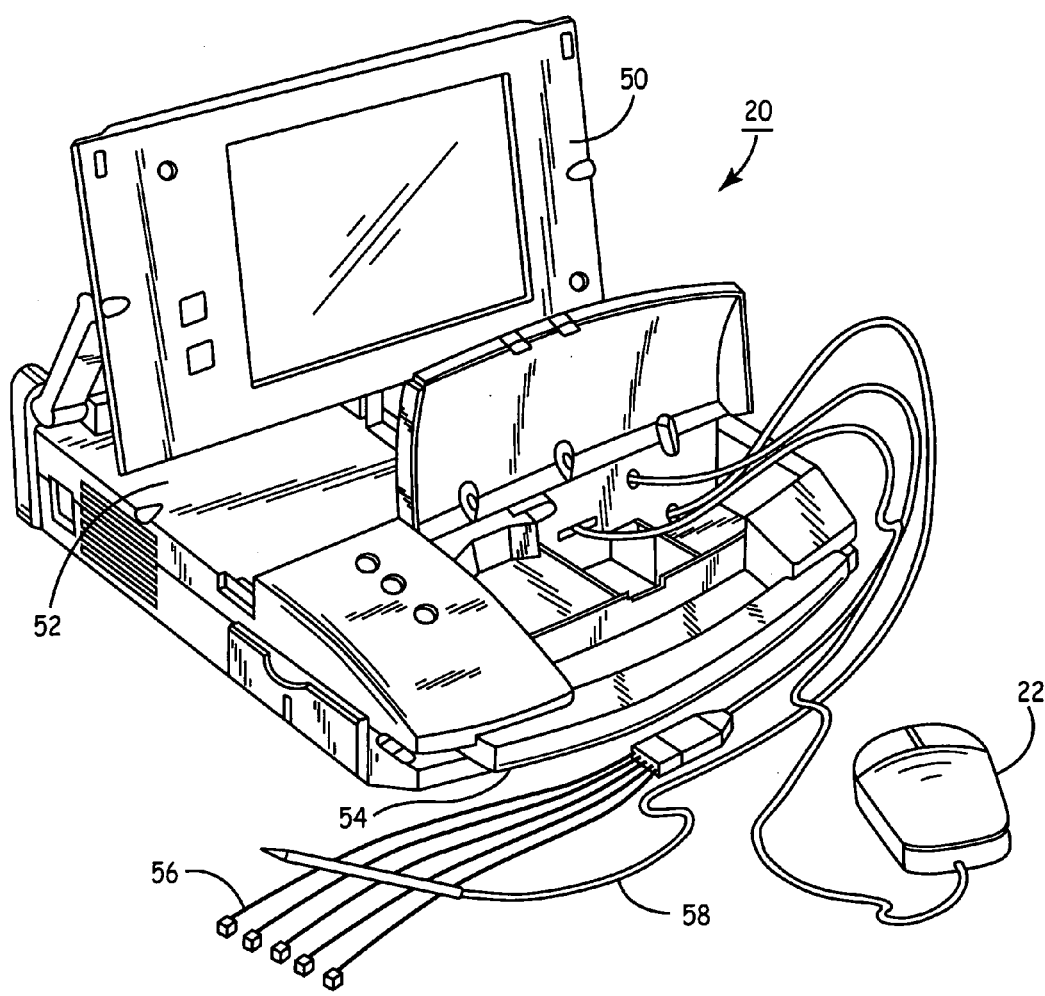
FIG. 2 is a view of the external programming unit of FIG. 1.

In FIG. 2, there is shown a perspective view of programming unit 20 in accordance with known practice in the prior art. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 52, which is preferably made of thermal plastic or another suitably rugged yet relatively lightweight material. A carrying handle, designated generally as 54 in FIG. 2, is integrally formed into the front of housing 52. With handle 54, programmer 20 can be carried like a briefcase.

An articulating display screen 50 is disposed on the upper surface of housing 52. Display screen 50 folds down into a closed position (not shown) when programmer 20 is not in use, thereby reducing the size of programmer 20 and protecting the display surface of display 50 during transportation and storage thereof.

A floppy disk drive is disposed within housing 52 and is accessible via a disk insertion slot (not shown). A hard disk drive is also disposed within housing 52, and it is contemplated that a hard disk drive activity indicator, (e.g., an LED, not shown) could be provided to give a visible indication of hard disk activation.

Those with ordinary skill in the art would know that it is often desirable to provide a means for determining the status of the patient's conduction system. Normally, programmer 20 is equipped with external ECG leads 54. It is these leads which are rendered redundant by the present invention.

In accordance with prior art practice, programmer 20 is equipped with an internal printer (not shown) so that a hard copy of a patient's ECG or of graphics displayed on the programmer's display screen 50 can be generated. Several types of printers, such as the AR-100 printer available from General Scanning Co., are known and commercially available.

In the perspective view of FIG. 2, programmer 20 is shown with articulating display screen 50 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 50 is operatively coupled to the computer circuitry disposed within housing 52 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
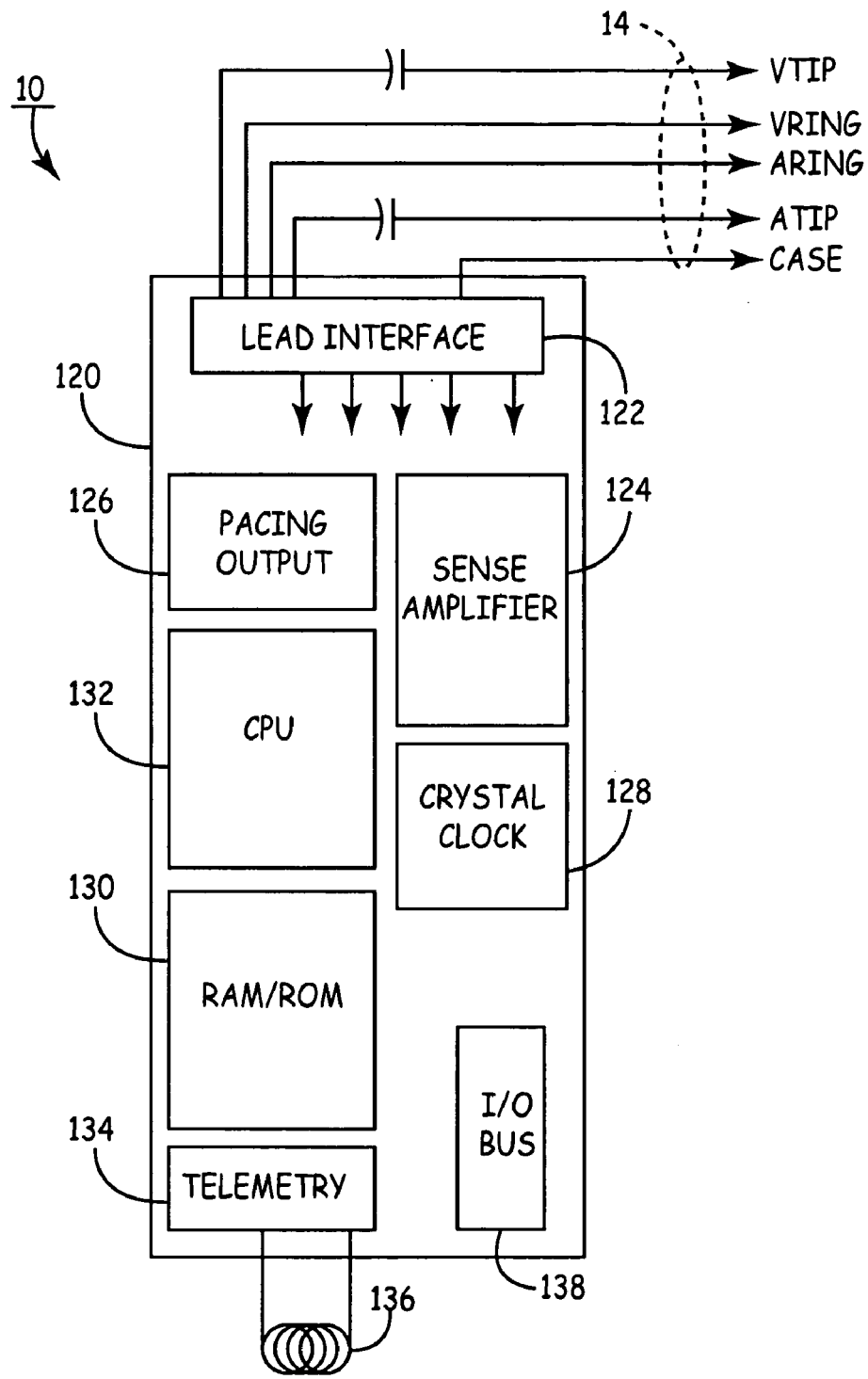
FIG. 3 is a block diagram of the body-implantable system of FIG. 1.

FIG. 3 is a block diagram of the electronic circuitry that makes up IMD 10 in accordance with the present invention. As can be seen from FIG. 3, IMD 10 comprises a primary stimulation control circuit 120 for controlling the device's pacing and sensing functions. The circuitry associated with stimulation control circuit 120 may be of conventional design, in accordance, for example, with what is disclosed U.S. Pat. No. 5,052,388 issued to Sivula et al., "Method and apparatus for implementing activity sensing in a pulse generator." To the extent that certain components of IMD 10 are conventional in their design and operation, such components will not be described herein in detail, as it is believed that design and implementation of such components would be a matter of routine to those of ordinary skill in the art. For example, stimulation control circuit 120 in FIG. 3 includes sense amplifier circuitry 124, stimulating pulse output circuitry 126, a crystal clock 128, a random-access memory and read-only memory (RAM/ROM) unit 130, and a central processing unit (CPU) 132, all of which are well-known in the art.

IMD 10 also includes internal communication circuit 134 so that it is capable of communicating with external programmer/control unit 20, as described in FIG. 2 in greater detail.

With continued reference to FIG. 3, IMD 10 is coupled to one or more leads 14 which, when implanted, extend transvenously between the implant site of IMD 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of IMD 10 may be facilitated by means of a lead interface circuit 122 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of IMD 10, as would be familiar to those of ordinary skill in the art. For the sake of clarity, the specific connections between leads 14 and the various components of IMD 10 are not shown in FIG. 3, although it will be clear to those of ordinary skill in the art that, for example, leads 14 will necessarily be coupled, either directly or indirectly, to sense amplifier circuitry 124 and stimulating pulse output circuit 126, in accordance with common practice, such that cardiac electrical signals may be conveyed to sensing circuitry 124, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 120 includes central processing unit 132 which may be an off-the-shelf programmable microprocessor or micro controller, but in the present invention is a custom integrated circuit. Although specific connections between CPU 132 and other components of stimulation control circuit 120 are not shown in FIG. 3, it will be apparent to those of ordinary skill in the art that CPU 132 functions to control the timed operation of stimulating pulse output circuit 126 and sense amplifier circuit 124 under control of programming stored in RAM/ROM unit 130. It is believed that those of ordinary skill in the art will be familiar with such an operative arrangement.

With continued reference to FIG. 3, crystal oscillator circuit 128, in the presently preferred embodiment a 32,768-Hz crystal controlled oscillator, provides main timing clock signals to stimulation control circuit 120. Again, the lines over which such clocking signals are provided to the various timed components of IMD 10 (e.g., microprocessor 132) are omitted from FIG. 3 for the sake of clarity.

It is to be understood that the various components of IMD 10 depicted in FIG. 3 are powered by means of a battery (not shown) which is contained within the hermetic enclosure of IMD 10, in accordance with common practice in the art. For the sake of clarity in the Figures, the battery and the connections between it and the other components of IMD 10 are not shown.

Stimulating pulse output circuit 126, which functions to generate cardiac stimuli under control of signals issued by CPU 132, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing defibrillation, cardioversion or combinations thereof output circuits that would be suitable for the purposes of practicing the present invention.

Sense amplifier circuit 124, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 132 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that IMD 10 may include numerous other components and subsystems, for example, activity sensors and associated circuitry. The presence or absence of such additional components in IMD 10, however, is not believed to be pertinent to the present invention, which relates primarily to the implementation and operation of communication subsystem 134 in pacemaker 10, and an associated communication subsystem in external unit 20.

The disclosure hereinabove relates to prior art practice in which programmer unit 20 is in telemetry communication with IMD 10 via telemetry head 22. Generally, access to the data contained in IMD 10 is obtained through programming unit 20. As can be seen from the prior art FIG. 1, this arrangement would require the patient to visit the doctor where the IMD data could be uplinked to programming unit 20 so that the physician or healthcare provider is able to review, for example, without limitations, EGM data including time intervals between sensed and paced events and signal morphologies, such that the physician is enabled to look at therapy and diagnostic data that has been recorded in IMD 10 over a period of time.

Figure 4:
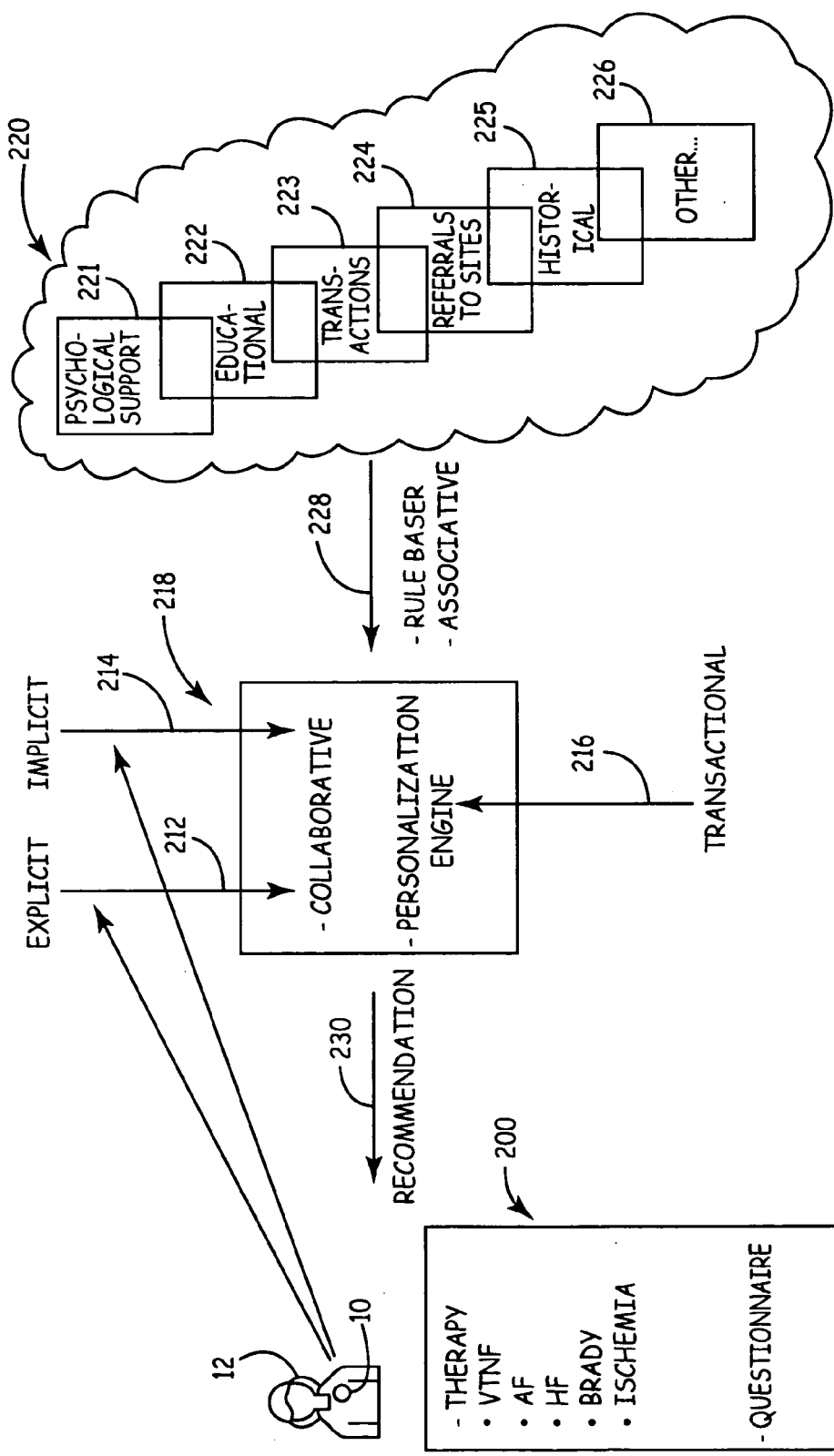
FIG. 4 is a representation of the interactivity between a personalization engine, an implanted device and a data server in communication therewith.
Figure 5:
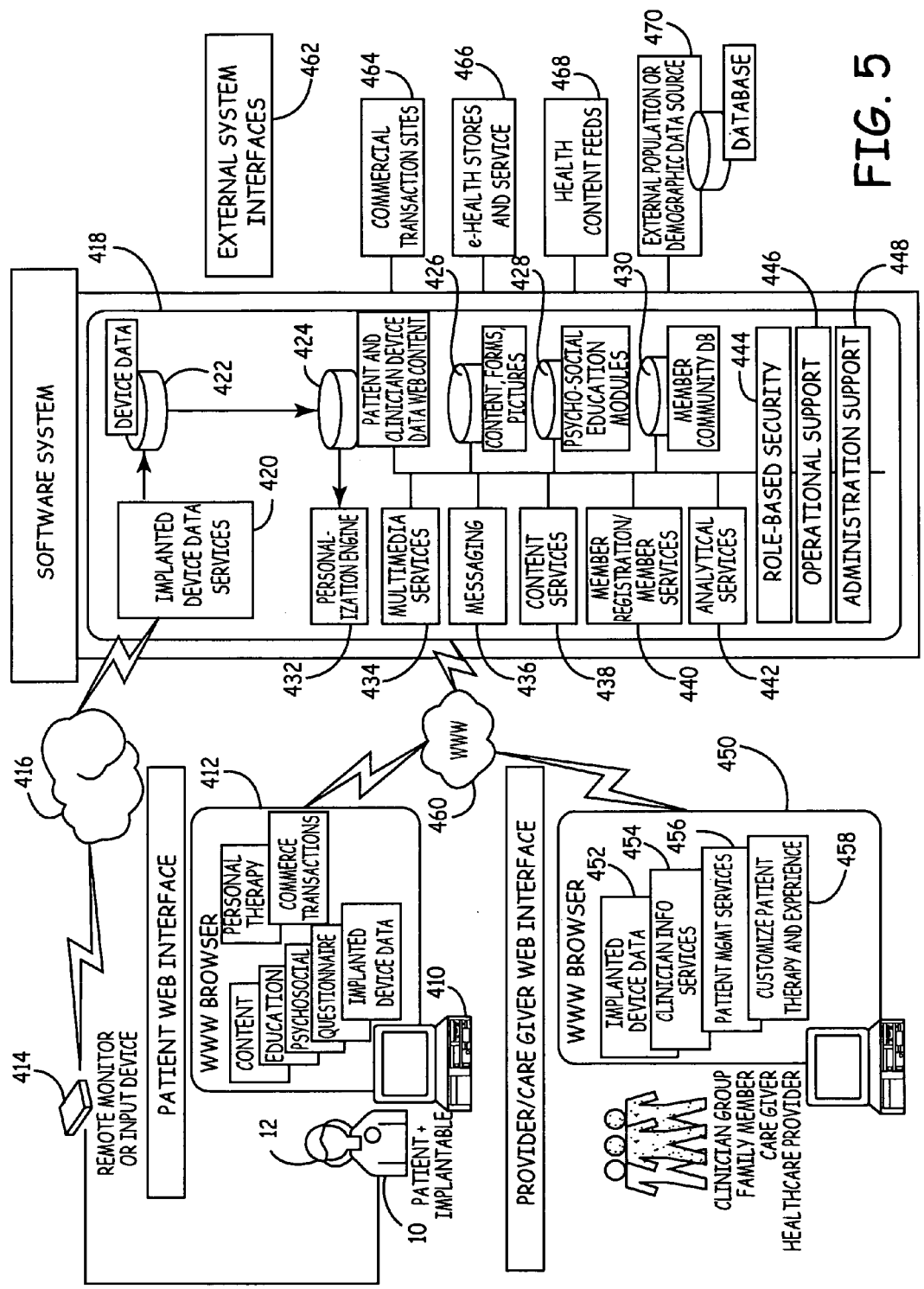
FIG. 5 is a representation of the medical device and the personalization engine connecting to various resources to provide comprehensive patient management system, including special services tailored to the patient.

In sharp contrast, the present invention provides a high level interaction between a patient, a physician, an implanted device, and other support groups by implementing a remote monitor that may be placed in the patient's home. More specifically, as represented in FIG. 4, in one aspect of the invention IMD 10 interacts with server 200 in a personalization scheme of a web experience by patient 12. Preferably, patient 12 interacts with a web browser at server 200, which web browser interacts with a website. Specifically, as patient 12 interacts through a browser with website 200, the website 218 into which a personalization engine is built, monitors the interaction that patient 12 is having and looks at the keystrokes, the mousestrokes or the explicit data 212 coming in. The personalization engine generally starts by checking explicit interactions 212 that the patient 12 is having and based on explicit interactions 212, the personalization engine may pull up certain background data for patient 12. For example, patient 12 may want to look at an educational module on atrial fibrillation and the personalization engine will find that in the library and present it out on the browser.

The personalization engine also looks for implicit data 214, which is based on drawing a conclusion. If patient 12 is offered the opportunity, for example, to look at atrial fibrillation information or ventricular fibrillation information, and the person chooses atrial fibrillation, the personalization engine may conclude that the person is more interested in atrial fibrillation than ventricular fibrillation, and this forms the basis of a conclusion. In transaction input 216, the specific type of explicit data that requires drawing a conclusion is considered. For example, if patient 12 looks at three articles or specific contents of a web and prints out one of them, that printing could be considered a transaction. Hence, recommendation 230 derived from the personalization engine would draw the conclusion that the article or the web content for some reason was more important or more relevant to patient 12 than the other portions of the presented articles.

Personalization engines can operate on a number of different principles, the most common ones being rule-based 228 or collaborative filtering 228. In collaborative filtering 228, the personalization engine is in contact with large databases of other users and is looking at what other users have found interesting. Thus, the personalization engine tries to make recommendations based on looking at specific interactions of patient 12, compares them to group norms, and draws conclusions about what else might be interesting for patient 12.

One aspect of the present invention includes the use of data input into the personalization engine using IMD 10 as a source of the data input. Specifically, data that is harvested out of IMD 10 includes its own interface into website 218 separate from the browser. More specifically, data from IMD 10 comes in through a separate system, but ultimately is delivered to the personalization engine and becomes a new input data. Accordingly, a keystroke or a mouse activity becomes integrated with IMD 10 and subsequently becomes input to the personalization engine, which operates in the manner described hereinabove. For example, if IMD 10 recorded data shows that patient 12 has had multiple episodes of atrial fibrillation and no episodes of ventricular fibrillation, the personalization engine may call up information on atrial fibrillation for patient 12 independent from patient 12 requesting the website to provide information on atrial fibrillation. Specifically, based on IMD 10 data, the personalization engine recognizes that atrial fibrillation is the disease that patient 12 suffers from and therefore recognizes it as something that patient 12 would be interested in. The website would have to deal with potential conflicting information. For example, if patient 12 wanted to learn about ventricular fibrillation, and data from IMD 10 shows that patient 12 is suffering from atrial fibrillation, the system would provide a different recommendation 230 to patient 12 based on whether there is concordance between entered data, IMD 10 data or discordance between them. Accordingly, the present invention enables to compile and assess data and information that patient 12 does not have access to and would be able to direct patient 12 to pertinent data, educational modules, links or other interventions that are more relevant to patient 12 in alignment with therapy and clinical data obtained from IMD 10.

Accordingly, the present invention provides a software-based system including a diagnostic component and a therapeutic component. The diagnostic component is designed to detect and identify psychosocial issues that a person has about their implanted medical device or underlying cardiologic problems. The therapeutic component provides a variety of tools and solutions that the person can use to help them deal with these stresses and issues. The invention is particularly suited for use in a networked computer system like the internet.

The diagnostic function of the system would use at least four different sources of input. First would be answers to explicit questions coming from patient 12 via explicit question input 212 based on a system-generated questionnaire that the person may fill out. Typically, the questions are designed to detect areas of psychosocial stress. Additional explicit data 212, such as input from healthcare providers for patient 12, family members or other involved individuals, would be gathered by providing a separate application interface for the additional parties. The application would provide appropriate rule-based 228 services and access right. The system may also access external data sources with broad population and/or demographic data not necessarily limited to patient or healthcare data that may be used as a further implicit 214 data source. Rule-based or associative input 228 may be derived from server 220, which includes, without limitation, psychological support information 221, educational support information 222, transactional support information 223, referrals to other sites 224, historical data 225 and others 226. Further, integrated data from implanted device 10 may indicate additional psychological stresses such as arrhythmias or other cardiac disorders which would be important for the overall diagnostic algorithm. Additional data sources for the diagnostic functionality could also include implicit data 214 such as click-stream analysis of sites visited, books or products purchased that might indicate a specific interest or concern, and the like. More specifically, the system could broker or provide access to other systems, for example, commercial sites, to both facilitate personalized commerce or transaction 216 to patient 12 in addition to collecting implicit data 214. The diagnostic function would then operate on explicit data 212, implicit data 214 and interrogative device data 200 to detect and identify areas of psychosocial concerns based on a set of rules, heuristics or correlative algorithms as is well known in the art.

Many different psychosocial diagnostic scenarios can be imagined. For example, sexual activity is a major area of concern for patients with implanted cardioverter defibrillators (ICDs). Nearly fifty percent of ICD patients report concern that sexual activity will trigger an ICD shock. The diagnostic function could detect whether this a concern for a specific patient by analyzing explicit data 212 based on a specific questionnaire regarding sexual activity. Further, implicit data 214 based on click-streams on websites dealing with sexual activity for ICD patients and interrogated device data 200, may infer the occurrence of shocks or arrhythmias during periods of time or during activity relating to sexual activity. Additional psychosocial diagnostic functionality from interrogative device data 200 that will be available from additional senses may include ischemia information, hemodynamic information, respiratory information and the like. The therapeutic component of the system uses the diagnostic information to generate a specific set of interventions to help the patient deal with the identified psychosocial issues.

Referring to FIG. 4, patient 12 will use PC 410 to access patient web interface 412. Patient web interface 412 includes IMD data questionnaires, psychosocial information, education, personal therapy information, commerce transaction and other content presented to patient 12 via the browser. Further, IMD 10 may be in wireless communication with a remote monitor or input device 414 to transfer data from IMD 10 to remote site via a network, for example, dial-up or the internet 416. Information that is collected from implanted medical device 10 via monitor 414 in network 416 is stored in server 418. Server 418 includes a software system configured to manage various databases.

Specifically, server 418 includes IMD services 420 with access to device data 422. Patient and clinician device data web content 424 is in data communication with device data storage 422 and personalization engine 432. Further, content, forms and pictures database 426, psychosocial education modules 428, member/community database 430 are in data communication with each other and also with multimedia services 434, messaging 436, content services 438, member registration/member services 440, and analytic services 442.

These databases and systems are also layered to communicate with rule-based security system 444, operational support 446 and registration support 448.

The present invention also provides server 450 dedicated to caregiver web interface. Server 450 includes, without limitation, IMD data 452, clinician information services 454, patient management services 456, and a site for customization of patient therapy and experience 458. Furthermore, the system includes external interfaces 462, including but not limited to, commercial transactions sites 464, e-health stores and service 466, health contents feeds 468 and external publication or demographic data source 470.

Accordingly, patient 12 is enabled to have access to information systems that are diversely populated to provide various services. Hence, what has been described above is a novel and inventive system to provide psychosocial support for patients based on explicit answers to questions and responses acquired therefrom. The system utilizes a robust web interface and browser to enable personalization engines that make recommendations based on the patient's individual interactions with various questionnaires. As an example, the data from IMD 10 in the patient is chronically monitored and that information is fed into a central server where data from the device may be compared with other patient and clinician data to provide various useful information and recommendation to the patient. Furthermore, the patient is enabled to connect with clinician groups, family members, caregivers and healthcare providers, thereby having universal access to data and communities of interest. Various changes may be made in the function and arrangement described in connection with the exemplary embodiments without departing from the scope of the invention as set forth in the appended claims.

What is claimed is:

1. A computer-implemented system providing on-line support to a patient having an implanted medical device (IMD), the system comprising:
   a website resident on a server;
   a patient interface to the website including a browser providing patient interaction with the website;
   an IMD interface to the website, through a system separate from the browser of the patient interface, permitting harvesting of data collected within the IMD;
   a personalization engine resident on the website for accepting a collection of implicit and explicit patient data obtained from said patient via the patient interface, obtaining collected data from said IMD via the IMD interface, and integrating patient data with collected IMD data from a plurality of IMDs of other patients to provide patient interaction with the website that results in patient access to pertinent patient support information based on the patient data input by the patient and the collected IMD data from the plurality of IMDs of other patients; and
   a data communication scheme providing data communications between said personalization engine and said patient and IMD interfaces.

2. The system of claim 1 wherein said pertinent information, to which said patient is provided access, is related to a commercial transaction.

3. The system of claim 1 wherein said pertinent information, to which said patient is provided access, is educational.

4. The system of claim 1 wherein said personalization engine further integrates, with said collected IMD data, data collected from individuals associated with said patient via a provider care giver interface.

5. The system of claim 1, wherein said data collected from said patient comprises responses to a questionnaire.

6. The system of claim 1, wherein said IMD interface comprises a home monitor in data communication with said IMD.

7. The system of claim 1, wherein the personalization engine provides the patient interaction based on whether there is concordance or discordance between the explicit data and the collected data from the patient's IMD.

8. The system of claim 1, further comprising:
databases storing psychological support information, educational support information, transactional support information, referrals to other websites, and historical data from which said pertinent information is provided.

9. A personalization system for implanted medical device patients, comprising:
a patient web interface to a website for collecting explicit patient data, implicit patient data, and transactional data;
an IMD interface to the website, through a remote monitor separate from the patient web interface, permitting harvesting of data collected within the IMD;
at least one external data source system interface;
a caregiver web interface; and
a server including a software system configured to manage multiple databases and interfaces; the server comprising:
a personalization engine to provide patient specific information based on the databases and interfaces,
wherein the databases store psychological support information, educational support information, transactional support information, referrals to other websites, and historical data.

10. The personalization system of claim 9, wherein the at least one external data source system interface include at least one of the group of commercial transaction sites, e-health stores and services, health content feeds, and external population or demographic data sources.

11. A personalization system for on-line support of a patient with implanted medical device (IMD), comprising:
a diagnostic component, wherein explicit patient data, implicit patient data, transactional data, patient IMD data, and external data sources are analyzed in a software system to detect and identify psychosocial issues for the patient, and wherein diagnostic information is generated; and
a therapeutic component, wherein the diagnostic information is used to generate a set of psychosocial interventions for the patient,
wherein the external data sources include commercial transaction sites, e-health stores and services, health content feeds, and external population/demographic data sources.

12. A method of providing on-line support for a patient having an implanted medical device (IMD), the method comprising:
retrieving recorded data from the IMD through an input device;
transferring the recorded data from the input device to a server through a network;
collecting patient based implicit and explicit data;
transferring the patient based implicit and explicit data through a patient web interface separate from the network for transferring the recorded data from the IMD to the server;
accessing external data sources based on the recorded data and implicit and explicit data;
generating a recommendation based on a personalization engine conclusion, the personalization engine conclusion based on whether there is concordance or discordance between the explicit data and the recorded data from the IMD; and
directing the recommendation to the patient.

13. The method of claim 12, wherein the patient implicit and explicit data is collected through an interrogative device.

14. The method of claim 12, wherein the personalization engine further generates a recommendation based on transactional input.

15. The method of claim 12, wherein the personalization engine operates on rule-based principles.

16. The method of claim 12, wherein the personalization engine operates on collaborative filtering.

17. The method of claim 12, wherein the external data sources include at least one of the group of psychological support information, educational support information, referrals to other sites, historical data and other patient's IMD data.

18. A computer-implemented system providing on-line support for a patient having an implanted medical device (IMD), the system comprising:
recorded data from the patient's IMD;
patient based implicit data and explicit data;
psychological support information, educational support information, transactional support information, referrals to websites, and historical data; and
a personalization engine configured to integrate the recorded data with the patient based implicit data and explicit data to form a personalization engine conclusion, and generate a support recommendation based on the personalization engine conclusion and at least one of the psychological support information, educational support information, transactional support information, referrals to websites, and historical data,
wherein the personalization engine conclusion is based on whether there is concordance or discordance between the explicit data and the recorded data from the patient's IMD.

19. The system of claim 18, comprising:
transactional data; and
wherein the personalization engine further collaborates the transactional data with the recorded data, patient based implicit data and explicit data to form the personalization engine conclusion.

* * * * *